United States Patent [19]
Urbahns et al.

[11] Patent Number: 6,103,925
[45] Date of Patent: Aug. 15, 2000

[54] DIMETHYL-SUBSTITUTED CYCLOHEXANE DIENE DERIVATIVES

[75] Inventors: Klaus Urbahns, Wuppertal; Frank Mauler, Overath, both of Germany

[73] Assignee: Bayer Aktiengesellschaft, Leverkusen, Germany

[21] Appl. No.: 09/155,187

[22] PCT Filed: Mar. 17, 1997

[86] PCT No.: PCT/EP97/01328

§ 371 Date: Sep. 22, 1998

§ 102(e) Date: Sep. 22, 1998

[87] PCT Pub. No.: WO97/36853

PCT Pub. Date: Oct. 9, 1997

[30] Foreign Application Priority Data

Mar. 29, 1996 [DE] Germany .................. 196 12 645

[51] Int. Cl.$^7$ .................................. C07C 69/76
[52] U.S. Cl. .................. 560/83; 560/51; 560/76; 560/21; 560/118; 560/127; 562/500; 562/509; 564/156; 564/169; 564/191; 514/532; 514/533; 514/545; 514/574

[58] Field of Search .................. 560/51, 76, 83, 560/118, 127, 21; 562/500, 509; 564/156, 169, 191; 514/532, 533, 545, 574

[56] References Cited

FOREIGN PATENT DOCUMENTS 87-18906  8/1987  United Kingdom .
8719441   8/1987  United Kingdom .

OTHER PUBLICATIONS

Abstract of JP 02–00129A.
Chemical and Pharmaceutical Bulletin, vol. 39, No. 11, Nov. 1991, Tokyo JP, pp. 2915–2923, XP002033122; Kazuhiko Take et al.: Agents for the Treatment of Overactive Detrusor.I.Synthesis and Structure–Activity Relationships of 1,1'–Biphenyl Derivatives.

*Primary Examiner*—Paul J. Killos
*Attorney, Agent, or Firm*—Norris, McLaughlin & Marcus, P.A.

[57] ABSTRACT

The present invention relates to dimethyl-substituted cyclohexanediene derivatives, to a process for their preparation, to their use as pharmaceuticals and to corresponding pharmaceuticals.

6 Claims, No Drawings

DIMETHYL-SUBSTITUTED CYCLOHEXANE DIENE DERIVATIVES

The present invention relates to dimethyl-substituted cyclohexanediene derivatives, to a process for their preparation and to their use as pharmaceuticals.

It has already been disclosed that 3,6-cyclohexanediene-2-phenyl-1,3-dicarboxylic esters have a muscle contraction-inhibiting effect [compare in this connection Chem. Pharm. Bull., 39 (11), 2915-23, 1991; GB 87-18906 870810/GB 87-19441 870817].

The invention relates to dimethyl-substituted cyclohexanediene derivatives of the general formulae (Ia,b)

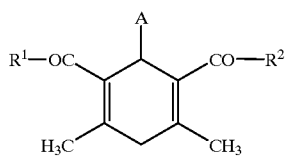

(Ia)

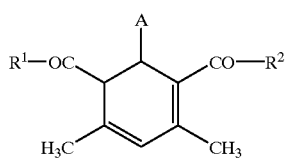

(Ib)

in which
A represents cycloalkyl having 3 to 6 carbon atoms or represents aryl having 6 to 10 carbon atoms, each of which are optionally substituted up to 3 times, identically or differently, by nitro, cyano, cycloalkyl having 3 to 7 carbon atoms, halogen, trifluoromethyl or by straight-chain or branched alkylthio, alkyl or alkoxy, each having up to 6 carbon atoms,
$R^1$ and $R^2$ are identical or different and
represent hydrogen or straight-chain or branched alkyl or alkoxy each having up to 8 carbon atoms, hydroxyl or represent a group of the formula —$NR^3R^4$,
in which
$R^3$ and $R^4$ are identical or different and
denote hydrogen, aryl having 6 to 10 carbon atoms or a straight-chain or branched alkyl having up to 4 carbon atoms,
and their salts.

Preferred salts are physiologically acceptable salts. These are generally salts of the compounds according to the invention with inorganic or organic acids. Preferred salts are those with inorganic acids such as, for example, hydrochloric acid, hydrobromic acid, phosphoric acid or sulphuric acid, or salts with organic carboxylic or sulphonic acids such as, for example, acetic acid, maleic acid, fumaric acid, malic acid, citric acid, tartaric acid, lactic acid, benzoic acid, or methanesulphonic acid, ethanesulphonic acid, phenylsulphonic acid, toluenesulphonic acid or naphthalenedisulphonic acid.

The compounds according to the invention may exist in stereoisomeric forms which are related either as image and mirror image (enantiomers), or which are not related as image and mirror image (diastercomers). The invention relates both to the antipodes and to the racemic forms, and to the mixtures of diastereomers. The racemic forms can, just like the diastereomers, be separated in a known manner into the stereoisomerically pure constituents.

Compounds of the general formula (Ia,b)
in which
A represents cyclohexyl, phenyl or naphthyl, each of which are optionally substituted up to 3 times, identically or differently, by nitro, cyano, fluorine, chlorine, bromine, iodine, cyclopentyl, cyclohexyl, trifluoromethyl or by straight-chain or branched alkylthio, alkyl or alkoxy each having up to 4 carbon atoms,
$R^1$ and $R^2$ are identical or different and
represent hydrogen or straight-chain or branched alkyl or alkoxy each having up to 6 carbon atoms, hydroxyl or represent a group of the formula —$NR^3R^4$,
in which
$R^3$ and $R^4$ are identical or different and
denote hydrogen, phenyl or straight-chain or branched alkyl having up to 3 carbon atoms,
and their salts, are preferred.

Compounds of the general formula (Ia,b)
in which
A represents cyclohexyl or phenyl, each of which are optionally substituted up to 3 times, identically or differently, by nitro, cyano, fluorine, chlorine, bromine, iodine, trifluoromethyl, cyclohexyl, methyl, methoxy or by methylthio,
$R^1$ and $R^2$ are identical or different and
represent hydrogen or straight-chain or branched alkyl or alkoxy each having up to 5 carbon atoms, hydroxyl or represent a group of the formula —$NR^3R^4$,
in which
$R^3$ and $R^4$ are identical or different and
denote hydrogen, phenyl, methyl or ethyl,
and their salts, are particularly preferred.

In addition, a process for preparing the compounds according to the invention of the general formulae (Ia) and (Ib) has been found, characterized in that
compounds of the general formula (II)

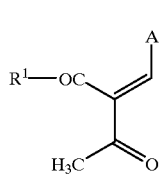

(II)

in which
A and $R^1$ have the abovementioned meanings are reacted with compounds of the general formula (III)

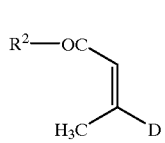

(III)

in which
$R^2$ has the abovementioned meanings,
D represents a radical of the formula $$CH_2-P(C_6H_5)_3{}^+E^- \text{ or } CH_2-P(O)(OR^5)(OR^6),$$

in which
$R^5$ and $R^6$ are identical or different and denote straight-chain or branched alkyl having up to 4 carbon atoms, E represents chloride or bromide, preferably represents bromide, in inert solvents, in the presence of a base, and in the case of the acids $R^1/R^2 \neq OH$ the esters are hydrolysed by customary methods, and in the case of the amides —CO—NH$_2$, starting from the acids are reacted with ammonium or the appropriate amines (NHR$^3$R$^4$), or starting from the corresponding esters of the cyclohexanediene derivatives of the general formula (Ia,b) an aluminium trimethyl-mediated aminolysis is carried out by the amines (NHR$^3$R$^4$) or their hydrochlorides.

The resulting double-bond isomers can be separated by chromatography and/or crystallization.

The process according to the invention can be explained by way of example by the following formula diagram:

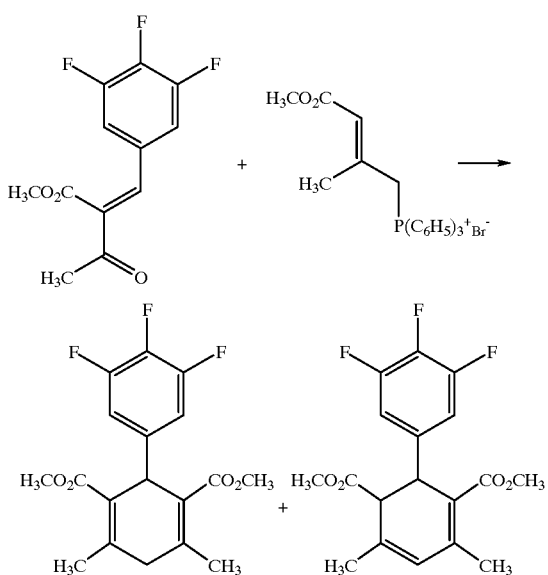

Suitable solvents are all inert organic solvents which are not changed under the reaction conditions. These preferably include alcohols such as methanol, ethanol, propanol or isopropanol, or ethers such as diethyl ether, dioxane, tetrahydrofuran, glycol dimethyl ether, or diethylene glycol dimethyl ether, acetonitrile, or amides such as hexamethylphosphoramide or dimethylformamide, or halogenated hydrocarbons such as methylene chloride, tetrachloromethane or hydrocarbons such as benzene or toluene, or pyridine. It is likewise possible to use mixtures of the said solvents. Methanol is preferred.

Suitable bases are inorganic or organic bases. These preferably include alkali metal hydroxides such as, for example, sodium hydroxide or potassium hydroxide, alkaline earth metal hydroxides such as, for example, barium hydroxide, alkali metal carbonates such as sodium carbonate or potassium carbonate, alkaline earth metal carbonates such as calcium carbonate, or alkali metal alcoholates such as, for example, sodium methanolate or sodium ethanolate or triethylamines or 1,8-diazabicyclo[5.4.0]undec-7-ene (DBU). Sodium methanolate is preferred.

The base is generally employed in an amount of from 0.1 mol to 100 mol, preferably from 1 mol to 10 mol, based on 1 mol of the compounds of the general formula (II).

The reaction temperatures may be varied within a relatively wide range. Those generally used are between +10° C. and +150° C., preferably between +20° C. and +100° C., in particular at room temperature.

The reactions can be carried out under atmospheric pressure but also under elevated or reduced pressure (for example 0.5 to 3 bar). Atmospheric pressure is generally used.

The carboxylic esters are hydrolysed by customary methods by treating the esters with customary bases in inert solvents.

Bases suitable for the hydrolysis are the customary inorganic bases. These preferably include alkali metal hydroxides or alkaline earth metal hydroxides such as, for example, sodium hydroxide, potassium hydroxide or barium hydroxide, or alkali metal carbonates such as sodium or potassium carbonate or sodium bicarbonate. Sodium hydroxide or potassium hydroxide are particularly preferably employed.

The hydrolysis can optionally also take place with acids such as, for example, trifluoroacetic acid, acetic acid, hydrochloric acid, hydrobromic acid, methanesulphonic acid, sulphuric acid or perchloric acid, preferably with trifluoroacetic acid.

Solvents suitable for the hydrolysis are water or the organic solvents customary for a hydrolysis. These preferably include alcohols such as methanol, ethanol, propanol, isopropanol or butanol, or ethers such as tetrahydrofuran or dioxane, or dimethylformamide or dimethyl sulphoxide. Alcohols such as methanol, ethanol, propanol or isopropanol are particularly preferably used. It is likewise possible to employ mixtures of the solvents mentioned.

The hydrolysis is generally carried out at a temperature in the range from 0° C. to +100° C., preferably from +20° C. to +80° C.

The hydrolysis is generally carried out under atmospheric pressure. However, it is also possible to operate under reduced pressure or elevated pressure (for example from 0.5 to 5 bar).

Solvents suitable for the amidation are the organic solvents which are listed above and which are not changed under the reaction conditions, with the ethers being preferred. Tetrahydrofuran is particularly preferred.

Suitable auxiliaries for the amidation with the compounds of the formula (IV) are carboduimides such as, for example, diisopropylcarbodiimde, dicyclohexylcarbodiimide or N-(3-dimethylaminopropyl)-N'-ethylcarbodiimide hydrochloride or carbonyl compounds such as carbonyldiimidazole or 1,2-oxazolium compounds such as 2-ethyl-5-phenyl- 1,2-oxazolium-3-sulphonate or propanephosphoric anhydride or isobutyl chloroformate or benzotriazolyloxytris (dimethylamino)phosphonium hexylfluorophosphate or diphenylphosphonyl amide or methanesulphonyl chloride or thionyl chloride, trifluoroacetic anhydride, optionally in the presence of bases such as triethylamine, pyridine or N-ethylmorpholine or N-methylpiperidine or dicyclohexylcarbodiimide and N-hydroxysuccinimide, alkoxycarbonyl-sulphonyltrialkylammonium hydroxides, acetic anhydride/NaOAc/phosphoric acid/mineral acids such as, for example, sulphuric acid or organic sulphonic acids such as, for example, p-toluenesulphonic acid. Thionyl chloride/pyridine is preferred.

Suitable auxiliaries for the amidation are generally organic sulphonic acids such as p-toluenesulphonic acid or anhydrous mineral acid such as phosphoric acid or sulphuric acid. p-Toluenesulphonic acid hydrate is preferred.

The auxiliary is employed in an amount of from 0.1 mol to 1 mol. preferably from 0.1 mol to 0.2 mol, in each case based on 1 mol of the compounds of the compounds to be amidated.

The aluminium trimethyl-mediated aminolysis is carried out in one of the solvents listed above, preferably in toluene at the reflux temperature.

The amidation can be carried out under atmospheric pressure but also under elevated or reduced pressure (for example 0.5 to 3 bar). Atmospheric pressure is generally used.

The compounds of the general formula (III) are known per se or can be prepared by customary methods.

The compounds of the general formula (II) are known or can be prepared, for example, by
reacting aldehydes of the general formula (IV)

  (IV)

in which
A has the abovementioned meanings,
with compounds of the general formula (V)

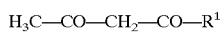  (V)

in which
$R^1$ has the abovementioned meanings,
in an organic solvent and in the presence of a base.

Suitable solvents are all inert organic solvents which are not changed under the reaction conditions. These preferably include alcohols such as methanol ethanol, propanol or isopropanol, or ethers such as diethyl ether, dioxane, tetrahydrofuran, glycol dimethyl ether, or diethylene glycol dimethyl ether, acetonitrile, or amides such as hexamethylphosphoramide or dimethylformamide, or acetic acid or halogenated hydrocarbons such as methylene chloride, tetrachloromethane or hydrocarbons such as benzene or toluene. It is likewise possible to use mixtures of the said solvents. Ethanol and methanol are particularly preferred.

Suitable bases are generally alkali metal hydrides or alcoholates such as, for example, sodium hydride or potassium tert-butoxide, or cyclic amines such as, for example, piperidine, dimethylaminopyridine or $C_1$–$C_4$-alkylamines such as, for example, triethylamine. Piperidine is preferred.

The reactions can be carried out under atmospheric pressure but also under elevated or reduced pressure (for example 0.5 to 3 bar). Atmospheric pressure is generally used.

The reaction temperatures can be varied within a relatively wide range. They are generally between +10° C. and +150° C., preferably between +20° C. and +100° C., in particular at the boiling point of the particular solvent.

The compounds of the general formula (IV) and (V) are known per se or can be prepared by customary methods.

The compounds according to the invention of the general formula (Ia,b) show a valuable range of pharmacological effects which could not be predicted.

They are modulators with selectivity for charybdotoxin-sensitive, calcium-dependent potassium channels (IK(Ca) channels), in particular of the central nervous system.

Because of their pharmacological properties, they can be employed for preparing pharmaceuticals for the treatment of central degenerative disorders, on the occurrence of dementias such as multiinfarct dementia (MID), primary degenerative dementia (PDD), presenile and senile dementia of the type of Alzheimer's disease, HIV dementia and other types of dementia, for the treatment of Parkinson's disease, amyotrophic lateral sclerosis and multiple sclerosis, cancer, restenosis and sickle cell anaemia.

The active substances are furthermore suitable for the treatment of brain dysfunctions in the elderly, of organic brain syndrome (OBS) and of age-associated memory impairment (AAMI).

They are suitable for the prophylaxis and control of the sequelae of disturbances of cerebral blood flow such as cerebral ischaemias, strokes, craniocerebral trauma and subarachnoid haemorrhages.

They are valuable for the treatment of depressions and psychoses, for example schizophrenia. In addition, they are suitable for the treatment of disorders of neuroendocrine secretion and of neurotransmitter secretion and health impairments associated therewith, such as mania, alcoholism, drug abuse, addiction or pathological eating behaviour. Further areas of use are the treatment of migraine, sleep disturbances and of neuropathies. They are also suitable as analgesics.

The active substances are furthermore suitable for the treatment of disorders of the immune system, in particular of T lymphocyte proliferation and for influencing smooth muscles, in particular of the uterus, urinary bladder and bronchial tract and for the treatment of disorders associated therewith, such as, for example, asthma and urinary incontinence and for the treatment of high blood pressure, arrhythmia, angina and diabetes.

Rubidium Efflux from C6-BU1 Glioma Cells

The experiments were carried out, with slight changes, in accordance with the method described by Tas et al. (Neurosci. Lett. 94, 279–284, (1988)). Rat C6-BU1 glioma cells are used for this. The increase in efflux caused by ionomycin above the baseline efflux is calculated from the data and set equal to 100%. The stimulations in the presence of test substances are then related to this value. Detection takes place by atomic absorption spectroscopy.

The present invention also includes pharmaceutical preparations which, besides inert, non-toxic, pharmaceutically suitable ancillary substances and excipients, contain one or more compounds of the general formulae (Ia) and (Ib), or which consist of one or more active substances of the formulae (Ia) and (Ib), and processes for producing these preparations.

The active substances of the formulae (Ia) and (Ib) should be present in these preparations in a concentration of from 0.1 to 99.5% by weight, preferably from 0.5 to 95% by weight, of the complete mixture.

Besides the active substances of the formulae (Ia) and (Ib), the pharmaceutical preparations may also contain other pharmaceutical active substances.

The pharmaceutical preparations mentioned above can be produced in a usual way by known methods, for example using the ancillary substance(s) or excipient(s).

It has generally proved advantageous to administer the active substance(s) of the formulae (Ia) and (Ib) in total amounts of about 0.01 to about 100 mg/kg, preferably in total amounts of about 1 mg/kg to 50 mg/kg, of body weight per 24 hours, where appropriate in the form of several single doses, to achieve the desired result.

However, it may, where appropriate, be advantageous to deviate from the stated amounts, in particular depending on the nature and body weight of the subject treated, on the individual behaviour towards the medicament, the nature and severity of the disorder, the nature of the preparation and administration, and the time or interval over which administration takes place.

PREPARATION EXAMPLES

Example 1 and Example 2

Dimethyl 2-(4-chloro-3-trifluoromethyphenyl)-4,6-dimethylcyclohexa-3,6-diene-1,5-dicarboxylate (Example 1)

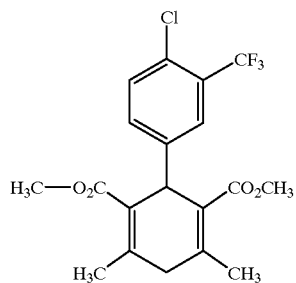

Dimethyl 2-(4-chloro-3-trifluoromethylphenyl)-4,6-dimethylcyclohexa-3,5-diene-1,5-dicarboxylate (Example 2)

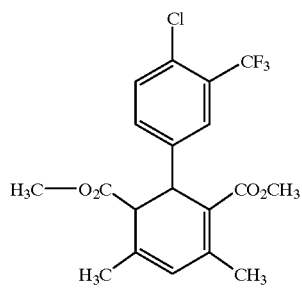

15.0 g (33 mmol) of 3-carboxymethyl-2-methylallyltriphenylphosphonium bromide are dissolved in 300 ml of dry methanol and, at 0° C., NaOCH$_3$ is added. After 1 h, 9.2 g (0.033 mol) of methyl 2-acetyl-3-(4-chloro-3-trifluoromethylphenyl)propenoate are added. The mixture is left to stand at room temperature for 2 h. The mixture is then acidified (pH =5) with acetic acid and concentrated. Taking up in methylene chloride is followed by washing with H$_2$O, drying and concentrating anew. Separation is then carried out by MPLC (methylene chloride/ethyl acetate =20:1) to result in 1.65 g of Example 1 and 5.18 g of Example 2.

Mp.: 91° C. (Example 1); Mp.: 104° C. (Example 2).

The compounds listed in Tables 1+2 are prepared in analogy to the method of Examples 1 and 2:

TABLE 1

| Ex. No. | A | R$^1$ | Mp. (° C.) |
|---|---|---|---|
| 3 | 3,4,5-trifluorophenyl | OCH$_3$ | 104 |
| 4 | 3,5-dichlorophenyl | OCH$_3$ | 150 |
| 5 | 3-nitrophenyl | OCH$_3$ | 129 |
| 6 | 4-chloro-3-nitrophenyl | OCH$_3$ | 145 |
| 7 | 4-fluoro-3-trifluoromethylphenyl | OCH$_3$ | 85 |
| 8 | 4-fluorophenyl | OCH$_3$ | 132 |
| 9 | 3-trifluoromethylphenyl | OCH$_3$ | 89 |
| 10 | cyclohexyl | OCH$_3$ | Oil |

TABLE 1-continued

[Structure: cyclohexadiene with R¹—O, A (wedge bond), COOCH₃, and two CH₃ groups]

| Ex. No. | A | R¹ | Mp. (° C.) |
|---|---|---|---|
| 11 | 4-Cl-3-CF₃-phenyl | OC(CH₃)₃ | Oil |
| 12 | 4-Cl-3-CF₃-phenyl | CH₃ | 89 |

TABLE 2

[Structure: cyclohexadiene with R¹—O, A, COOCH₃, and two CH₃ groups]

| Ex. No. | A | R¹ | Mp. (° C.) |
|---|---|---|---|
| 13 | 3,4,5-trifluorophenyl | OCH₃ | 105 |
| 14 | 3,5-dichlorophenyl | OCH₃ | 75 |
| 15 | 3-nitrophenyl | OCH₃ | 150 |
| 16 | 4-Cl-3-NO₂-phenyl | OCH₃ | 119 |
| 17 | 4-F-3-CF₃-phenyl | OCH₃ | 112 |
| 18 | 4-fluorophenyl | OCH₃ | 108 |
| 19 | 3-CF₃-phenyl | OCH₃ | 114 |
| 20 | cyclohexyl | OCH₃ | 95 |
| 21 | 4-Cl-3-CF₃-phenyl | OC(CH₃)₃ | Oil |

Example 22

4,6-Dimethyl-2-(4-chloro-3-trifluoromethylphenyl) cyclohexa-3,6-diene- 1,3-dicarboxylic acid monomethyl ester

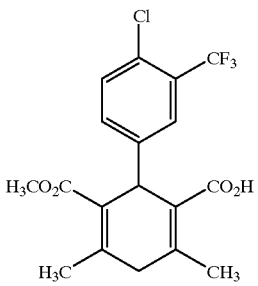

1.5 g (3.3 mmol) of the compound from Example 21 are dissolved in 50 ml of methylene chloride, and 5 ml of trifluoroacetic acid are added. Stirring at RT for 3 h results in 0.86 g of the title compound. Mp.: 165° C.

Example 23

Methyl 5-carbamoyl-2,4-dimethy,-6-(4-chloro-3-trifluoromethylphenyl)cyclohexa-1,4-diene-carboxylate

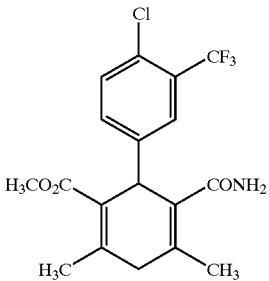

447 mg (1.15 mmol) of the compound from Example 22 are stirred with $SOCl_2$, under reflux for 2 h. After concentration the residue is dissolved in 10 ml of dry THF. The solution is added dropwise to 20 ml of $NH_3$/water at 0° C. The filtrate is substantially removed by distillation, and extraction is carried out 3× with ethyl acetate. Chromatography of the combined material (ethyl acetate/petroleum ether =2:1)) affords 152 mg of the title compound. Mp.: 153° C.

What is claimed is:

1. Cyclohexanediene derivatives of the general formula (Ia,b)

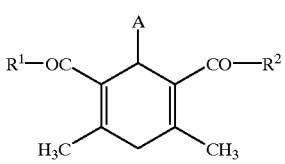

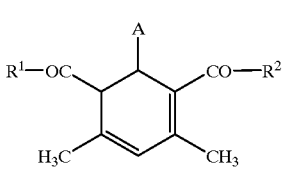

in which

A represents cycloalkyl having 3 to 6 carbon atoms or represents aryl having 6 to 10 carbon atoms, each of which are optionally substituted up to 3 times, identically or differently, by nitro, cyano, cycloalkyl having 3 to 7 carbon atoms, halogen, trifluoromethyl or by straight-chain or branched alkylthio, alkyl or alkoxy, each having up to 6 carbon atoms, $R^1$ and $R^2$ are identical or different and represent hydrogen or straight-chain or branched alkyl or alkoxy each having up to 8 carbon atoms, hydroxyl or represent a group of the formula —$NR^3R^4$, in which $R^3$ and $R^4$ are identical or different and denote hydrogen, aryl having 6 to 10 carbon atoms or a straight-chain or branched alkyl having up to 4 carbon atoms, and their salts.

2. Cyclohexanediene derivatives according to claim 1, characterized in that

A represents cyclohexyl, phenyl or naphthyl, each of which are optionally substituted up to 3 times, identically or differently, by nitro, cyano, fluorine, chlorine, bromine, iodine, cyclopentyl, cyclohexyl, trifluoromethyl or by straight-chain or branched alkylthio, alkyl or alkoxy each having up to 4 carbon atoms, $R^1$ and $R^2$ are identical or different and represent hydrogen or straight-chain or branched alkyl or alkoxy each having up to 6 carbon atoms, hydroxyl or represent a group of the formula —$NR^3R^4$, in which $R^3$ and $R^4$ are identical or different and denote hydrogen, phenyl or straight-chain or branched alkyl having up to 3 carbon atoms, and their salts.

3. Cyclohexane derivatives according to claim 1, characterized in that

A represents cyclohexyl or phenyl, each of which are optionally substituted up to 3 times, identically or differently, by nitro, cyano, fluorine, chlorine, bromine, iodine, trifluoromethyl, cyclohexyl, methyl, methoxy or by methylthio, $R^1$ and $R^2$ are identical or different and represent hydrogen or straight-chain or branched alkyl or alkoxy each having up to 5 carbon atoms, hydroxyl or represent a group of the formula —$NR^3R^4$, in which $R^3$ and $R^4$ are identical or different and denote hydrogen, phenyl, methyl or ethyl, and their salts.

4. Process for preparing cyclohexanediene derivatives according to claim 1, characterized in that compounds of the general formula (II)

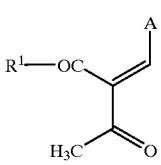

in which

A and $R^1$ have the meanings stated in claim 1 are reacted with compounds of the general formula (III)

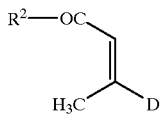 (III)

in which

R² has the meanings stated in claim 1,

D represents a radical of the formula

in which

R⁵ and R⁶ are identical or different and denote straight-chain or branched alkyl having up to 4 carbon atoms, E represents chloride or bromide, in inert solvents, in the presence of a base, and in the case of the acids $R^1/R^2 \neq$ OH the esters are hydrolysed, and in the case of the amides —CO—NH₂, starting from the acids are reacted with ammonia or the appropriate amines (NHR³R⁴), or starting from the corresponding esters of the cyclohexanediene derivatives of the general formula (Ia,b) an aluminium trimethyl-mediated aminolysis is carried out by the amines (NHR³R⁴) or their hydrochlorides.

5. Pharmaceutical containing at least one cyclohexanediene derivative according to claim 1 and a pharmaceutical carrier.

6. Pharmaceutical according to claim 5 as modulator with selectivity for charybdotoxin-sensitive, calcium-dependent potassium channels.

* * * * *